(12) United States Patent
Teague et al.

(10) Patent No.: US 8,845,599 B2
(45) Date of Patent: Sep. 30, 2014

(54) MEDICAL PROCEDURES, DEVICES AND KITS FOR THE FORMATION AND REMOVAL OF PLUG-FORMING COMPOSITIONS

(75) Inventors: James Teague, Spencer, IN (US); Mark Hera, Bloomington, IN (US)

(73) Assignee: Boston Scientific Scimed, Inc., Maple Grove, CA (US)

( * ) Notice: Subject to any disclaimer, the term of this patent is extended or adjusted under 35 U.S.C. 154(b) by 33 days.

(21) Appl. No.: 13/544,174

(22) Filed: Jul. 9, 2012

(65) Prior Publication Data
US 2013/0018314 A1 Jan. 17, 2013

Related U.S. Application Data

(60) Provisional application No. 61/506,318, filed on Jul. 11, 2011.

(51) Int. Cl.
A61M 25/00 (2006.01)
A61L 31/14 (2006.01)
A61L 31/06 (2006.01)
A61M 25/01 (2006.01)

(52) U.S. Cl.
CPC .......... *A61M 25/007* (2013.01); *A61L 2430/36* (2013.01); *A61M 25/0136* (2013.01); *A61L 31/14* (2013.01); *A61M 25/0147* (2013.01); *A61L 31/06* (2013.01); *A61M 2210/1078* (2013.01)

USPC .......................................... 604/264

(58) Field of Classification Search
USPC .......... 604/95.04, 102.01, 517; 606/127, 128
See application file for complete search history.

(56) References Cited

U.S. PATENT DOCUMENTS

| | | | | |
|---|---|---|---|---|
| 4,899,733 A | * | 2/1990 | DeCastro et al. | 600/104 |
| 5,203,772 A | * | 4/1993 | Hammerslag et al. | 604/528 |
| 7,137,966 B2 | | 11/2006 | Sahatjian et al. | |
| 7,837,672 B2 | * | 11/2010 | Intoccia | 604/540 |
| 7,955,315 B2 | * | 6/2011 | Feinberg et al. | 604/528 |
| 2005/0143678 A1 | | 6/2005 | Schwarz | |
| 2007/0088256 A1 | * | 4/2007 | Intoccia | 604/102.02 |
| 2007/0191768 A1 | | 8/2007 | Kolb | |
| 2008/0208163 A1 | | 8/2008 | Wilkie | |
| 2010/0274231 A1 | * | 10/2010 | Pravong et al. | 606/2.5 |
| 2011/0092957 A1 | * | 4/2011 | Intoccia | 604/540 |

OTHER PUBLICATIONS

Author unknown, Product Literature, "Backstop for Kidney Stone Removal,", 2 pages, downloaded from www.pluromed.com, on Jan. 6, 2011.

* cited by examiner

*Primary Examiner* — Aarti B Berdichevsky
(74) *Attorney, Agent, or Firm* — Kacvinsky Daisak Bluni PLLC

(57) ABSTRACT

The present description relates to plug-forming compositions, to medical procedures employing such compositions, to methods for removing such compositions, and to products pertaining to such compositions, including medical devices, medical device components, and kits, among other aspects.

21 Claims, 4 Drawing Sheets

MEDICAL PROCEDURES, DEVICES AND KITS FOR THE FORMATION AND REMOVAL OF PLUG-FORMING COMPOSITIONS

STATEMENT OF RELATED APPLICATION

This application claims the benefit of U.S. Ser. No. 61/506,318, filed Jul. 11, 2011 and entitled "MEDICAL PROCEDURES, DEVICES AND KITS FOR THE FORMATION AND REMOVAL OF PLUG-FORMING COMPOSITIONS," which is hereby incorporated by reference in its entirety.

FIELD OF THE INVENTION

The present invention relates to plug-forming compositions, to medical procedures employing such compositions, to methods for forming and removing such compositions, and to products pertaining to such compositions, including medical devices, medical device components, and kits, among other aspects.

BACKGROUND

Concretions can develop in certain parts of the body, such as in the kidneys, pancreas, ureter and gallbladder. It is common for biological concretions to be referred to as calculi or stones, especially when they are composed of mineral salts. For example, concretions formed in the biliary system are called gallstones. Those that form in the bladder are as also known as vesical calculi or bladder stones, and cystoliths. Calculi occurring in the kidney are often called kidney stones. Calculi can also occur in the ureter and are usually the result of the passage of stones originating in the kidney. Calculi are also present, for example, in salivary ducts or glands.

Lithotripsy is a popular, minimally invasive medical procedure that uses energy in various forms such as acoustic shock waves, pneumatic pulsation, electrical hydraulic shock waves, or laser beams to break up biological concretions. The force of the energy, when applied either extracorporeally or intracorporeally, usually in focused and continuous or successive bursts, comminutes a concretion into smaller fragments that may be extracted from the body or allowed to pass from the body.

There are several complications, however, which can result from lithotripsy. One problem with this procedure is that when concretions are fragmented, the fragments can become widely distributed. For example, when kidney stones are fragmented, the fragments can become widely distributed throughout the ureter and kidney. Therefore, during the procedure, it is desirable to confine the kidney stone and the resulting fragments within a constrained space. Various mechanical anti-migration backstops have been developed and involve the placement of these devices behind the kidney stone. Another approach, described in U.S. Patent Pub. No. 2005/0143678 involves the introduction of a temporary plug behind the stone, preventing the stone and its fragments from migrating further up the urethra or kidney.

SUMMARY

One aspect of the present disclosure relates to a medical device comprising an elongated body, a proximal end and a distal tip. The device also comprises a lumen whose proximal end terminates at the proximal end and whose distal end terminates at the distal tip. The proximal end is adapted to engage a source of fluid. The lumen is adapted to carry carrying the fluid from the proximal end to the distal tip of the device. The distal tip is adapted to reverse the flow direction of fluid emerging from the catheter such that fluid emerging from the distal tip flows in the direction of the proximal end of the device.

Another aspect of the present disclosure relates to kits comprising such a medical device.

Another aspect of the present disclosure relates to a method for removing a polymeric plug from a body lumen that is accessible from outside the body via a natural or man-made body opening. The lumen comprises a proximal end (the end closest to the body opening) and a distal end opposite the proximal end. The method comprises positioning a tip of a catheter at a position distal to the polymeric plug and directing a plug removal fluid from the catheter tip in a proximal direction (i.e., in the direction of the plug and the body opening). In this way, the polymeric plug-forming material and any other material positioned on the proximal side of the plug (e.g., concretions fragments from a lithotripsy procedure) are washed in the direction of the body opening (and typically out of the body opening), inhibiting the material from migrating further up the lumen during the plug removal process.

These and other aspects, embodiments and advantages of the present disclosure will become immediately apparent to those of ordinary skill in the art upon review of the Detailed Description and any claims to follow.

DETAILED DESCRIPTION

Figure 1A:
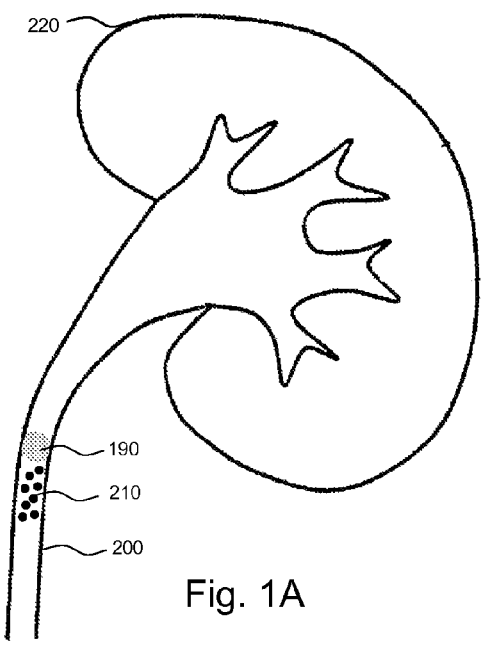
FIGS. 1A-1D schematically illustrate a method of removing a polymeric plug and concretion fragments, in accordance with an embodiment of the present disclosure.

One aspect of the present disclosure relates to a method for removing a polymeric plug from a body lumen, which lumen comprises a proximal end (i.e., an end through which fluid in the lumen can exit the body through a body opening, which opening may be natural or surgically formed) and a distal end opposite the proximal end. For example, in the case where the body lumen is a ureter, the proximal end of the ureter is the end of the ureter that is in fluid communication with the bladder and the distal end of the ureter is the end that is in fluid communication with the kidney. The method comprises positioning a tip of a catheter at a position distal to the polymeric plug and directing a plug removal fluid from the catheter tip in a proximal direction (i.e., in the direction of the plug). For example, in this method, more than 50 vol % of the fluid emerging from the tip preferably flows in the proximal direction. More preferably 75 vol % or more, 90 vol % or more, or even 95 vol % or more of the fluid emerging from the tip flows in the proximal direction. Typically, flow is continued until 50 vol % or more of the plug-forming material is removed (preferably 75 vol % or more, 90 vol % or more, or even 95 vol % or more of the plug-forming material). In this way, the polymeric plug-forming material and any material positioned on the proximal side of the plug (e.g., concretion fragments from a lithotripsy procedure) are washed in the direction of the exit from the body, inhibiting the material from migrating further up the lumen (e.g., further up the urethra and/or into the kidney).

As used herein, the term "lumen" denotes the space enclosed by a tube-like structure, such as a catheter, or a hollow body organ, such as inside an artery, a vein, a kidney, a gall bladder, a ureter, a urinary bladder, a pancreas, a salivary gland, a small intestine or a large intestine (i.e., an opening, space, or cavity in a biological system).

As used herein, "subjects" are vertebrate subjects, more typically mammalian subjects, including human subjects, pets and livestock.

The term "concretion" denotes a mass or nodule of solid matter formed in the body. Common synonyms, for example, are stones, clots, tones, lumps or calculi. Concretions can develop in certain parts of the body, such as in the kidneys, pancreas, ureter and gallbladder. It is common for biological concretions to be referred to as calculi or stones, especially when they are composed of mineral salts. For example, concretions formed in the biliary system are called gallstones. Those that form in the bladder are as also known as vesical calculi or bladder stones, and cystoliths. Calculi occurring in the kidney are often called kidney stones. Calculi can also occur in the ureter and are usually the result of the passage of stones originating in the kidney. It is also possible to observe the presence of calculi, for example, in salivary ducts or glands.

Larger biological concretions often need to be broken up because their size prohibits non-surgical removal from the body of a subject. Such a procedure is known as lithotripsy. Shattering a concretion (by, for example, light, chemical, or physical energy) can disperse the resulting fragments from the original location of the concretion. It is important to remove the fragments, as fragments that are not removed from the body can form the nuclei for the formation of new concretions. This process is made difficult by the fact that the shattering process often causes fragments to move into inaccessible or unknown areas of the body thus preventing or interfering with the capture and removal of the fragments. This problem can be addressed by injecting temporary plugs behind a concretion (e.g., in the case internal, or intracorporeal, lithotripsy), or in front and behind a concretion (e.g., in the case of external shock wave lithotripsy), prior to the fragmentation of the concretion.

The polymeric plug may be formed from a fluid plug-forming composition that increases in viscosity upon administration to a subject. A composition is "fluid" at a given temperature if it has the ability to flow when subjected to a shear stress. A fluid will assume the shape of its container over time. Such compositions include, for example, free flowing liquid compositions, as well as viscous, gel-like materials, that may be delivered to a desired site by injection (e.g., through a syringe, catheter, and so forth). Such plug-forming compositions may undergo an increase in viscosity, for instance, as a result of a change in environment at the administration site, for example, as a result of a change a change in temperature, pH, pressure or light level (e.g., infrared, ultraviolet, visible), or as a result of a chemical or biological reaction (e.g., a crosslinking reaction).

In certain embodiments, plug-forming compositions include those that increase in viscosity when warmed to body temperature (e.g., ~37° C. for humans) from a temperature below body temperature, for example, from a temperature within the range of 35° C. to 10° C. or less (e.g., 35° C. to 30° C. to 25° C. to 20° C. to 15° C. to 10° C. or less), including typical room temperatures of 20° C. to 30° C. (68° F. to 86° F.). Such compositions may also reversibly decrease in viscosity when subsequently cooled from body temperature to a temperature below body temperature (which temperature will depend on the nature of the plug-forming composition).

For example, in certain embodiments, a fluid plug-forming composition is injected into the body at a temperature below body temperature. As the composition equilibrates with the temperature of the body, the viscosity of the composition increases. In preferred embodiments, a plug-forming composition may be selected that increases in viscosity (e.g., an increase of five-fold or more, ten-fold or more, twenty-fold or more, one-hundred-fold or more, or even one-thousand-fold or more, among other possibilities) as the temperature rises to the body temperature of the subject from an introduction temperature that lies in a range from 10° C. or less to 35° C. (e.g., 10° C. or less to 15° C. to 20° C. to 25° C. to 30° C. to 35° C.), among other values. As a result of this increase in viscosity, a polymeric plug (also sometimes referred to as a gel plug) is formed.

Conversely, at a later time (e.g., after conducting a medical procedure), the temperature of the plug-forming composition may be reduced to below body temperature using a suitable technique, thereby rendering the plug-forming composition less viscous and thus more easily removed from the body. For instance, the composition may be exposed to cold water or cold saline (e.g., using a catheter), which, in addition to reducing the viscosity of the composition, may also have the effect of dissolving the composition.

Beneficial fluid plug-forming compositions include compositions that comprise so-called reverse thermosensitive polymers, also referred to as inverse thermosensitive polymers and reversibly gelling polymers. "Reverse thermosensitive," "inverse thermosensitive" and "reversibly gelling" refer to the property of a polymer wherein gelation (which is associated with an increase in viscosity) takes place upon an increase in temperature, rather than a decrease in temperature. "Transition temperature" refers to the temperature or temperature range at which gelation of a reverse thermosensitive polymer occurs.

Reverse thermosensitive polymers may be characterized in accordance with ASTM D-5133, which is incorporated by reference herein in its entirety. The measurements resulting from this test method are viscosity, the maximum rate of viscosity increase (the gelation index), and the temperature at which the gelation index occurs (the gelation temperature). Preferred gelation temperatures range from 30 to 37° C., among other possibilities.

In certain embodiments, the reverse thermosensitive polymer employed may be a block copolymer. The block copolymer may be a biodegradable, biocompatible block copolymer that comprises a polyoxyalkylene block, for example, a block copolymer comprising polyoxyethylene, blocks, polyoxypropylene blocks, or both polyoxyethylene and polyoxypropylene blocks.

In certain embodiments, the block copolymers employed have a number-average molecular weight (Mn) ranging from about 1,000 to 500,000 Daltons or more, for instance, from 1,000 to 2,000 to 5,000 to 10,000 to 20,000 to 50,000 to 100,000 to 200,000 to 500,000 Daltons or more. In certain embodiments, the polymer is in an aqueous solution. For example, aqueous solutions may contain about 5% to about 30% polymer, more typically about 10% to about 25% polymer.

The pH of reverse thermosensitive polymer solutions may vary widely, but preferably range from about 6.0 to about 7.8, which are suitable pH levels for injection into a mammalian body.

In certain embodiments, the reverse thermosensitive polymers used are poloxamers or poloxamines. Their viscosity increases and decreases with an increase and decrease in temperature, respectively. Several members of this class of polymer, including poloxamer 188, poloxamer 407, poloxamer 338, poloxamine 1107 and poloxamine 1307, show reverse thermosensitivity at or near the physiological temperature range. For instance, poloxamer 407 is a biocompatible polyoxypropylene-polyoxyethylene block copolymer having an average molecular weight of about 12,500 and a polyoxypropylene fraction of about 30%, whereas poloxamer 188 has an average molecular weight of about 8400 and a polyoxypropylene fraction of about 20%, poloxamer 338 (Pluronic™ F108) has an average molecular weight of about 14,600 and a polyoxypropylene fraction of about 20%, poloxamine 1107 has an average molecular weight of about 14,000 and poloxamine 1307 has an average molecular weight of about 18,000.

Polyoxypropylene-polyoxyethylene block copolymers that have these properties include polymers that are available commercially as Pluronic™ poloxamers and Tetronic™ poloxamines (BASF, Ludwigshafen, Germany) and generically known as poloxamers and poloxamines, respectively. Pluronic™ polymers have surfactant abilities and low toxicity and immunogenic responses. A specific example of such a polymer is described in Example of Pub. No. US 2008/0208163 to Wilkie, wherein LeGoo™ (poloxamer 407) at 20% aqueous concentration is used to close a femoral arteries of pigs.

For further information regarding reverse thermosensitive polymers, methods of purifying the same, and methods of modifying the transition temperature of the same, among other information, see US 2008/0208163 to Wilkie.

In addition to agents (e.g., polymers) that are responsible for increasing viscosity of the plug-forming compositions on admistration to a subject, plug-forming compositions in accordance with the present disclosure may further include a number of supplemental agents. For example, therapeutic agents and/or contrast-enhancing agents may be added to the compositions in some embodiments.

In this regard, in certain embodiments, to aid in visualization, a contrast-enhancing agent can be added to the plug-forming compositions described herein. Exemplarily contrast-enhancing agents are radiopaque materials, paramagnetic materials, heavy atoms, transition metals, lanthanides, actinides, dyes, and radionuclide-containing materials.

In certain embodiments, therapeutic agents, including a non-steroidal anti-inflammatory agents, steroids, analgesics and an antimicrobial agents, among others may be added to the plug-forming compositions described herein.

In various embodiments, plug-forming compositions like those described herein are used to isolate one part of the body from another part of the body during a medical procedure. For example, such compositions may be used to isolate concretion fragments arising from lithotripsy as noted above. Such compositions may also be used to block particle migration of polyps or tumor migration during laser treatment in an anatomic lumen wherein it is desirable to restrict movement of tissue, debris, and so forth, during a procedure.

As noted above, in certain embodiments, polymer solutions (e.g., aqueous or organic solutions) containing of one or more reverse thermosensitive polymers may be employed as plug-forming compositions. These polymer solutions are liquids below body temperature and viscous gels at body temperature. In various embodiments, the polymer solution is provided external of the body at a temperature below body temperature. The polymer solution may be further chilled to prolong the time the composition stays in the liquid form upon introduction into the body, in some embodiments. For example, the introduction temperature may be about 10° C. below the gelation temperature of the polymer solution, among other possibilities.

One aspect of the present disclosure relates to a method of lithotripsy comprising the steps of: injecting a first liquid plug-forming composition (e.g., one comprising an inverse thermosensitive polymer) into a lumen of a mammal on a first side of a concretion, wherein the first plug-forming composition preferably does not contact the concretion; and optionally injecting a second liquid plug-forming composition (e.g., one comprising an inverse thermosensitive polymer), which may be the same as the first liquid plug-forming composition, into the lumen on a side of the concretion opposite the first plug-forming composition. For example, in the case of a kidney stone in a ureter, the plug-forming composition may be introduced distal to the stone (or both distal and proximal to the stone) through a catheter. In one embodiment, a syringe or other pumping device (e.g., a pump selected from those listed below) may be used to inject an inverse thermosensitive polymer into the body via the catheter. For example, where a syringe is employed for delivery, pressure may be applied to the syringe by hand or by an automated syringe plunger. In one embodiment, a liquid plug-forming composition (e.g., BackStop™) maybe introduced, for example, using a BackStop™ injector and a BackStop™ catheter, which are available from Pluromed, Inc., Woburn, Mass., USA. After plug formation, energy is directed to the concretion causing the concretion to fragment into a plurality of fragments.

Although plug-forming compositions that increase in viscosity upon administration to a subject (e.g., reverse thermosensitive polymers) are preferred as described herein, as will be appreciated by those of ordinary skill in the art, in certain embodiments, plug-forming compositions (e.g., gels, etc.) may be employed which are sufficiently viscous under delivery conditions to isolate one part of the body from another part of the body during a medical procedure. (Due to their viscosities, such compositions may require higher pressures to deliver them than the temperature sensitive plug-forming compositions described elsewhere herein.)

An aspect of the present disclosure relates to a method for removing a plug-forming material in the form of a polymeric plug from a body lumen that is accessible from outside the body via a natural or man-made body opening. The lumen comprises a proximal end (the end closest to the body opening) and a distal end opposite the proximal end. (For instance, in the case where the body lumen is a ureter, the proximal end of the ureter is the end of the ureter which is in fluid communication with the bladder and the distal end of the ureter is the end which is in fluid communication with the kidney.) The method comprises positioning a tip of a catheter at a position distal to the polymeric plug (or the most distal polymeric plug, where a plurality of polymer plugs are present) and directing a plug removal fluid from the catheter tip in a proximal direction (i.e., toward the bladder and away from the kidney, in the direction of the plug). For example, in this method, more than 50 vol % of the fluid emerging from the tip preferably flows in the proximal direction. More preferably 75 vol % or more, 90 vol % or more, or even 95 vol % or more of the fluid emerging from the tip flows in the proximal direction. Typically, flow is continued until 50 vol % or more of the plug material is removed (preferably 75 vol % or more, 90 vol % or more, or even 95 vol % or more of the plug material). Examples of plug removal fluids include non-aqueous solutions and aqueous solutions (e.g., water, saline, etc.).

By the above technique, the plug-forming material and any material positioned on the proximal side of the plug (e.g., concretions fragments from a lithotripsy procedure, additional plugs proximal to the concretions, etc.) are washed in the direction of the exit from the body, inhibiting the material from migrating further up the lumen (e.g., further up the urethra and/or into the kidney).

Figure 1B:
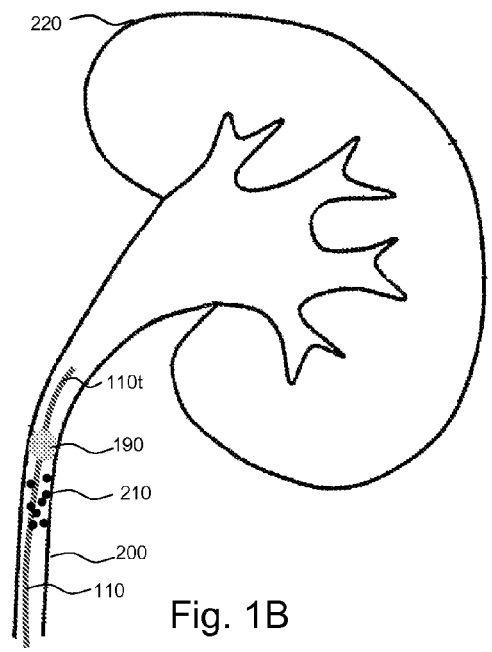

Referring now to a specific embodiment shown in FIGS. 1A-1D, in FIG. 1A there is shown a kidney 220 and a ureter 200, within which are present a polymeric plug 190 and the concretion fragments 210 arising from a previously performed lithotripsy procedure. As shown in FIG. 1B, a catheter 110 in accordance with the present disclosure is inserted into the ureter and through the polymer plug 190 to a position where the distal tip 110t of the catheter lies distal to the plug 190.

The catheters used in the present disclosure for this purpose typically range, for example, from 1 to 1.5 to 2 to 2.5 to 3 to 3.5 to 4 to 4.5 French in diameter, and from 90 to 150 mm in length, among other values.

Materials for the catheters of the present disclosure include fluorocarbon polymers such as polytetrafluoroethylene (PTFE) and fluorinated ethylene propylene (FEP) polymers, polyolefins such as polyethylene, poly(ethylene-co-vinyl acetate) (EVA), and polyurethanes, among others.

Where fluoroscopic guidance is employed, the catheter may be compounded with radiopaque materials or marked with such materials (e.g., via marker bands). Examples of radiopaque materials include metals, metal salts and metal oxides, and iodinated compounds. More specific examples of such agents include gold, tungsten, platinum, tantalum, iridium, or other dense metal, barium sulfate, bismuth subcarbonate, bismuth trioxide, bismuth oxychloride, metrizamide, iopamidol, iothalamate sodium, iodomide sodium, and meglumine, among others.

In other embodiments the catheter may be advanced from the working channel of a scope (e.g., ureter scope) with visual guidance.

Figure 1C:
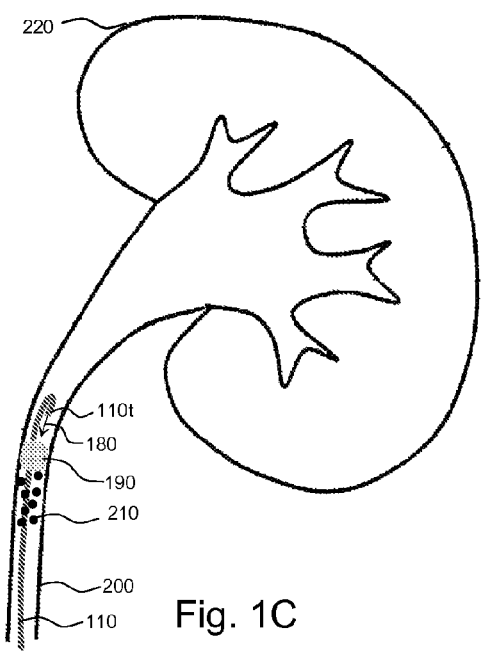

In the embodiment shown in FIG. 1C, the distal tip 110t is then formed into a shape (e.g., a "u shape") that causes fluid flowing from the catheter tip to flow in a proximal direction. Subsequently, a plug removal fluid (whose flow is designated by arrow 180) is forced through the catheter and out the distal tip 110t of the catheter in order to remove the material forming the plug 190 and at the same time flush part or all of the concretion fragments 210 from the ureter as shown in FIG. 1D.

In some embodiments, the end of the catheter tip may be provided with a perforated member (e.g., a spray head, etc.) (not shown) for distributing the plug removal fluid over a greater area.

Figure 1D:
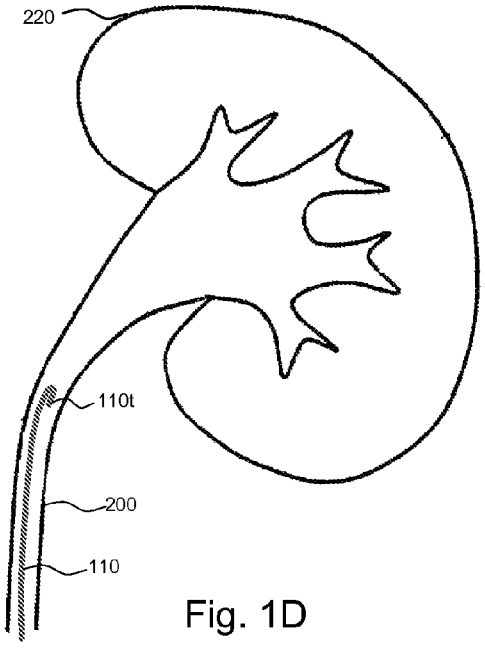
Figure 2:
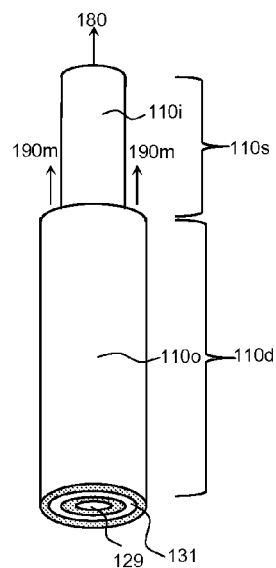
FIG. 2 is a schematic illustration of a transition region from a dual lumen portion to a single lumen portion of a catheter in accordance with an embodiment of the present disclosure.

The catheter 110 shown in the embodiment of FIGS. 1B-1D can be a single lumen device in which the single lumen is used to deliver the plug removal fluid 180 from the catheter tip. In other embodiments, the catheter may be a multi-lumen device. For example, in the embodiment shown in FIGS. 2A-2C, a catheter having a dual lumen portion 110d and a single lumen portion 110s is employed. The portion of the catheter in which a transition from the single lumen portion 110s to the dual lumen portion 110d occurs is shown in FIG. 2. As seen from this figure, the dual lumen portion 110d contains an inner catheter tube 110i and an outer catheter tube 110o, whereas the single lumen portion 110s contains only the inner catheter tube 110i. The dual lumen portion 110d contains (a) a central lumen 129 (within inner catheter tube 110i) for delivery of the plug removal material and (b) an outer annular lumen 131 (between the inner catheter tube 110i and the outer catheter tube 110o) for delivery of a plug-forming material 190m.

Figure 2A:
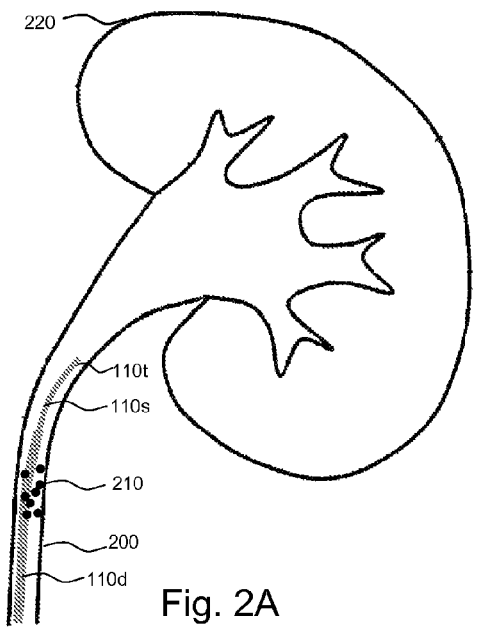
FIGS. 2A-2C schematically illustrate a method of forming and removing a polymeric plug, in accordance with an embodiment of the present disclosure.
Figure 2B:
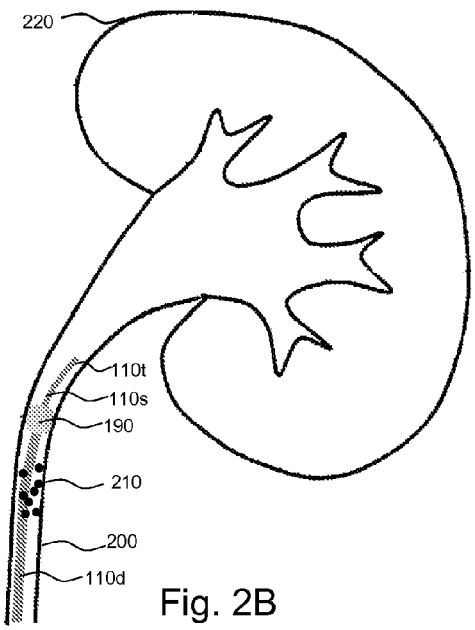
Figure 2C:
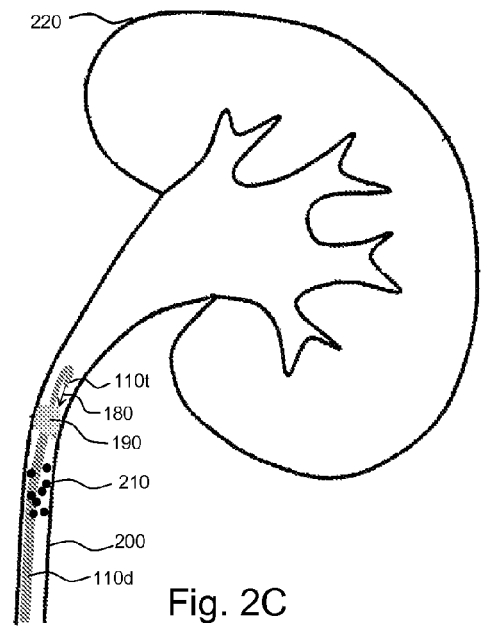

When positioned within the ureter 200 as shown in FIG. 2A, a plug-forming material 190m may be introduced through the outer lumen 131 (as shown in FIG. 2) for form a plug 190 as shown in FIG. 2B. Subsequently, a plug removal fluid 180 can be directed toward the proximal end of the catheter 110 (i.e., retrograde flow) as shown by directional arrow in FIG. 2C, for example, by inverting the distal tip 110t into a shape (e.g., a "u shape") that causes that causes fluid flowing from the catheter tip to flow in a proximal direction (as shown in FIG. 2C) or by using another type of retrograde flow tip as discussed below.

In one embodiment, the distal tip is formed with an intrinsic shape (e.g., an intrinsic "u-shape") that causes that causes fluid flowing from the catheter tip to flow in a proximal direction, for example by bending the tip of the catheter and heat treating the tip to maintain the bended shape in the absence of any applied force. In other words, the distal tip is provided with a shape memory, with the distal tip returning to the memorized shape in the absence of an applied force. Such a device may be, for example, advanced over a guide wire (which holds the tip in a relatively linear form) to the desired position in the body (e.g., ureter) after which the guide wire is withdrawn from the tip, allowing the shape of the tip to return to its intrinsic shape.

Figure 3A:
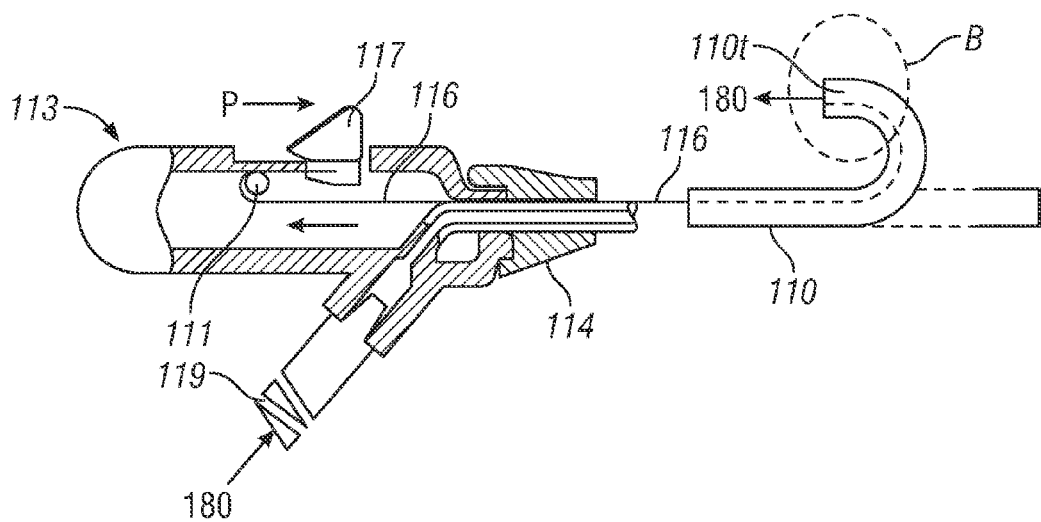
FIG. 3A is a schematic illustration of a catheter in accordance with an embodiment of the present disclosure.
Figure 3B:
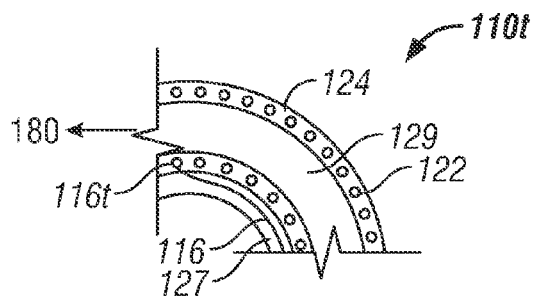
FIG. 3B is a schematic illustration of an enlarged view of region B in FIG. 3A.

In other embodiments, the catheter is provided with a mechanism for deforming the distal tip into a shape causes that causes fluid flowing from the catheter tip to flow in a proximal direction (i.e., retrograde flow). For example, turning now to FIG. 3A, in another embodiment, a pull-wire 116 extends from a handle 113, along the length of the catheter, to near the catheter tip 110t. For example, the pull-wire 116 can be routed over a pulley 111 to a thumb tab 117. By pushing the thumb tab 117 in direction P, the pull-wire 116 is retracted from the distal tip of the catheter 110t, bending the distal tip into a u-shape as shown. The handle 113 further includes a tubing strain relief member 114 and an inlet port 119 (e.g., a female or male luer lock port) through which plug removal fluid 180 can be introduced (e.g., via an apparatus with a opposite male or female luer lock exit port) and forced to the distal tip 110t. As shown in more detail in FIG. 3B, which is an enlarged view of region B in FIG. 3A, the catheter also includes a metallic spring coil 122 which reinforces the polymeric shaft material 124 in the embodiment shown. For example, the spring coil can be embedded between polymeric layers (e.g., polyimide layers, PTFE layers, etc.). The pull wire 116 may be attached to distal tip of the spring coil 122 (designated as point 116t) at a distal tip of the catheter 110t. As shown, the catheter includes a central lumen 129 for delivery of the plug removal fluid 180 and a pull wire lumen 127 which extends proximally to the handle within which movement of the pull wire 116 is permitted.

Plug removal fluid may be fed to the inlet port of the catheter by various means, including the use of a simple elevated container of fluid (e.g., a drip bag, etc.). In other embodiments, the plug removal fluid is introduced via a pump. Examples of pumps which may be employed for this purpose include positive displacement pumps such as rotary-type positive displacement pumps and reciprocating-type positive displacement pumps, for instance, rotary lobe pumps, progressing cavity pumps, rotary gear pumps, screw pumps, gear pumps, roots-type pumps, hydraulic pumps, vane pumps, regenerative (peripheral) pumps, peristaltic pumps, piston pumps, syringe pumps, and diaphragm pumps, velocity pumps, for instance, centrifugal pumps, radial flow pumps, axial flow pumps, mixed flow pumps and eductor-jet pumps, as well as buoyancy pumps, impulse pumps and gravity pumps, among others.

In one specific embodiment, a vacuum-syringe-based system with check valves, such as the SAPS™—Single Action Pumping System available from Boston Scientific Corporation, Natick, Mass., USA, may be employed to pump the plug removal fluid.

Figure 4A:
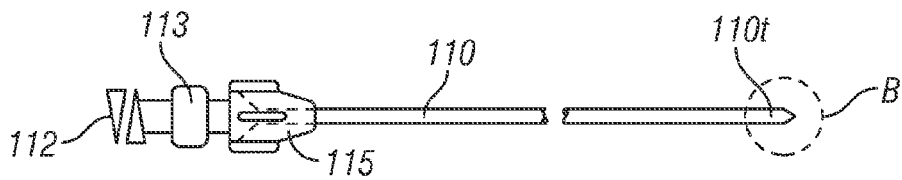
FIG. 4A is a schematic illustration of a catheter in accordance with an embodiment of the present disclosure.

In another embodiment of the disclosure, the catheter tip is provided with a retrograde flow tip which reverses the direction of the fluid as it exits the tip of catheter without the need to bend the tip. Turning now to FIG. 4A there is shown a catheter handle 113 which includes a luer connector 112 as an inlet port and a catheter connecting cap 115 from which catheter shaft 110s emerges. As shown in more detail in FIG. 4B, which is an enlarged view of region B in FIG. 4A, the catheter tip 110t includes four apertures 110a, positioned at 90° angles around the circumference of the tip 110t, which result in a reversal in direction between the fluid 180i entering the tip 110t and the fluid 180o that exits the tip 110t. Consequently the fluid 180o flows in an overall retrograde (i.e., proximal) direction relative to the direction (i.e., distal) of the fluid 180i entering the tip 110t.

Figure 4B:
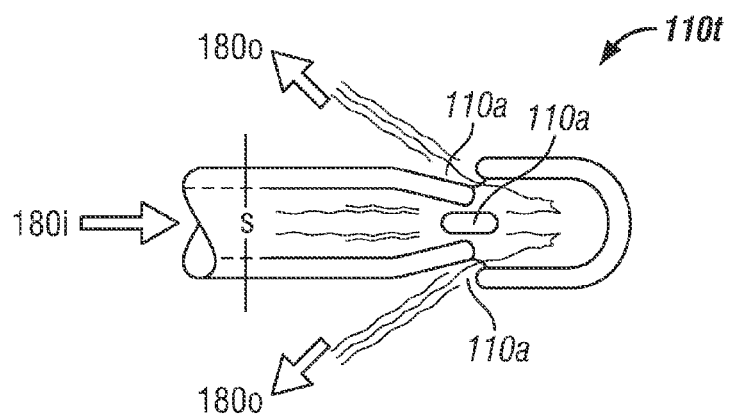
FIG. 4B is a schematic illustration of an enlarged view of region B in FIG. 4A.
Figure 5:
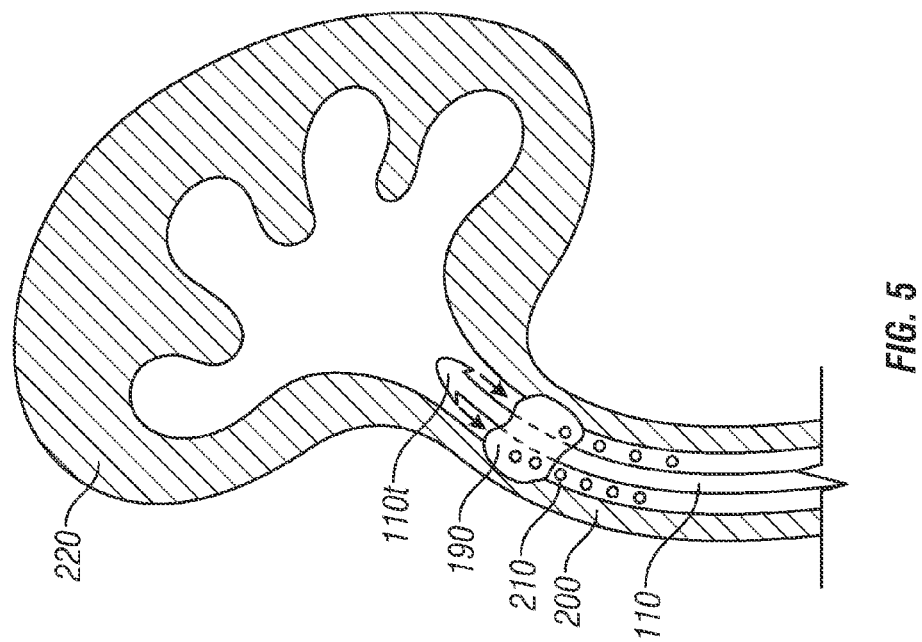
FIG. 5 schematically illustrates a method of removing a polymeric plug and nearby concretion fragments, in accordance with an embodiment of the present disclosure.

A catheter like that of FIGS. 4A-4B is shown in FIG. 5, wherein there is shown a kidney 220 and a ureter 200, within which is present a polymeric plug 190 as well as concretion fragments 210 arising from a previously performed lithotripsy procedure. The catheter 110 has been inserted into the ureter 200 and through the polymer plug 190 to a position where the distal tip 110t of the catheter lies distal to the plug 190. A plug removal fluid is forced through the catheter and out the distal tip 110t of the catheter in order to remove the plug 190 and flush part or all of the concretion fragments 210 from the ureter. Due to the design of the catheter tip 110t, the fluid flows out of the tip 110t in a retrograde direction (i.e., proximally, as shown by arrows) relative to the fluid 180i entering the tip 110t (i.e., the fluid flow is distal within the catheter until it reaches the tip 110t).

Figure 6A:
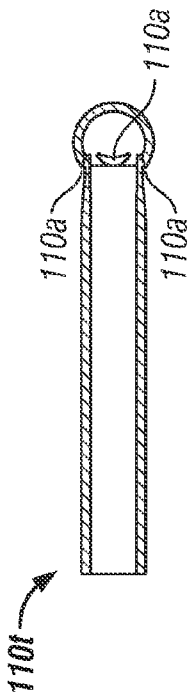
FIG. 6A is a cross section of the catheter tip of FIG. 6B taken along line A-A.
Figure 6B:
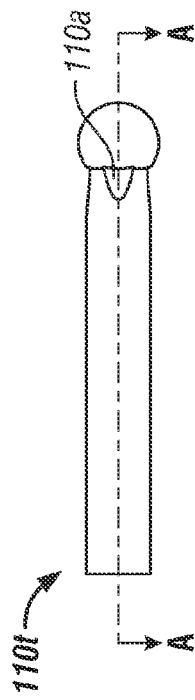
FIG. 6B is a schematic illustration of a catheter tip with in accordance with an embodiment of the present disclosure.

FIG. 6B is an illustration of a catheter tip 110t with in accordance with an embodiment of the present disclosure that includes four apertures 110a positioned at 90° angles around the circumference of the tip 110t, which result in a reversal in direction between the fluid entering the tip and the fluid that exits the tip 110t. FIG. 6A is a cross section of the catheter tip of FIG. 6B taken along line A-A. Although four apertures 110a are show, clearly other numbers of apertures may be employed (e.g., one, two, three, five, six, seven, eight, etc.).

Such apertures form reverse angled conduits to direct the fluid flow toward the proximal end of the catheter and are significantly smaller openings than the ID or inner lumen of the catheter (e.g., 30 to 60% of the ID). This allows pressure to build in the distal closed end of the catheter and provides increased fluid flow in the reverse direction.

Figure 7A:
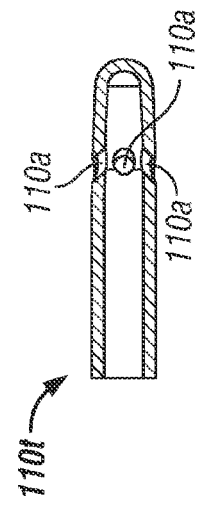
FIG. 7A is a cross section of the catheter tip of FIG. 7B taken along line A-A.
Figure 7B:
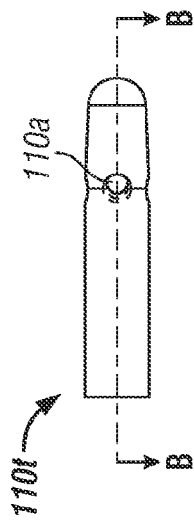
FIG. 7B is a schematic illustration of a catheter tip with in accordance with an embodiment of the present disclosure.

FIG. 7B is an illustration of a catheter tip 110t in accordance with an embodiment of the present disclosure that includes four apertures 110a positioned at 90° angles around the circumference of the tip 110t, which result in a reversal in direction between the fluid entering the tip and the fluid that exits the tip 110t. FIG. 7A is a cross section of the catheter tip of FIG. 6B taken along line A-A. Although four apertures 110a are show, clearly other numbers of apertures may be employed.

In other embodiments of the disclosure, kits are provided which contain any combination of two or more of the following items: (a) a catheter that is adapted for retrograde fluid flow at the tip (see the various embodiments discuss above in conjunction with the figures), (b) a plug-forming material (e.g., a reverse thermosensitive polymer composition), (c) a pump (e.g., a syringe pump), (d) plug removal fluid (e.g., water, saline, etc.), (e) a guidewire, (f) a suitable packaging material and (g) printed material (e.g., a label) comprising one or more of the following: (i) storage information and (ii) instructions regarding how to administer the fluid plug-forming material and/or the plug removal fluid.

Various aspects of the invention relating to the above are enumerated in the following paragraphs.

Aspect 1. A medical device comprising an elongated body, a proximal end, a distal tip, and a lumen extending from the proximal end of the device to the distal tip of the device, wherein the proximal end of the device is adapted to engage a source of fluid, wherein the lumen is adapted to carry carrying the fluid from the proximal end of the device to the distal tip of the device, and wherein the distal tip of the device is adapted to cause fluid emerging from the distal tip of the device to flow in the direction of the proximal end of the device.

Aspect 2. The medical device of aspect 1, wherein the diameter of the catheter is dimensioned for insertion into a ureter.

Aspect 3. The medical device of aspect 2, wherein the catheter is between 1 and 4.5 Fr in diameter.

Aspect 4. The medical device of aspect 1, wherein the distal tip has a shape memory in the form of a u-shape.

Aspect 5. The medical device of aspect 1, comprising a pull wire which is adapted to form a u-shaped distal tip for the catheter when pulled.

Aspect 6. The medical device of aspect 5, wherein the pull wire disposed within a second lumen that extends along a portion of the length of the elongate body.

Aspect 7. The medical device of aspect 5, wherein the distal tip comprises a spring coil.

Aspect 8. The medical device of aspect 5, wherein the pull wire is attached to the spring coil.

Aspect 9. The medical device of aspect 1, wherein the distal tip comprises a plurality of exit ports each of which expels fluid in a proximal direction.

Aspect 10. The medical device of aspect 1, further comprising a second lumen which is adapted for delivery of a fluid plug-forming composition.

Aspect 11. The medical device of aspect 1, wherein the proximal end of the device comprises a luer lock fluid entry port.

Aspect 12. The medical device of aspect 1, wherein the proximal end of the device comprises a handle.

Aspect 13. A kit comprising (a) the medical device of aspect 1 and (b) a pump.

Aspect 14. A kit comprising (a) the medical device of aspect 1 and (b) a guidewire.

Aspect 15. A kit comprising (a) the medical device of aspect 1 and (b) a reverse thermosensitive polymer.

Aspect 16. The kit of aspect 15, wherein the reverse thermosensitive polymer is a block copolymer that comprises a polyoxyalkylene block.

Aspect 17. The kit of aspect 15, wherein the reverse thermosensitive polymer is a block copolymer that comprises polyoxyethylene, blocks, polyoxypropylene blocks, or both polyoxyethylene blocks and polyoxypropylene blocks.

Aspect 18. A method comprising (a) positioning the medical device of aspect 1 within a body lumen that contains a polymeric plug, such that the distal tip of the device is positioned on a distal side of the polymeric plug, (c) forcing a plug removal fluid through the lumen and out the distal tip of the device such that fluid emerging from the distal tip of the device flows in the direction of the polymeric plug such that it dissolves the polymeric plug.

Aspect 19. The method of aspect 18, wherein the plug comprises a reverse thermosensitive polymer.

Aspect 20. The method of aspect 18, wherein the plug removal fluid is saline.

Aspect 21. The method of aspect 18, wherein the body lumen is a ureter.

Although various embodiments are specifically illustrated and described herein, it will be appreciated that modifications and variations of the present disclosure are covered by the above teachings and are within the purview of the appended claims without departing from the spirit and intended scope of the disclosure.

The invention claimed is:

1. A medical device comprising an elongated body, a proximal end, a distal tip, a first lumen extending from the proximal end of the device to the distal tip of the device, and a second lumen which is adapted for delivery of a fluid plug-forming composition to a subject, wherein the proximal end of the device is adapted to engage a source of plug removal fluid, wherein the first lumen is adapted to carry the plug removal fluid from the proximal end of the device to the distal tip of the device, and wherein the distal tip of the device is adapted to cause plug removal fluid emerging from the distal tip of the device into the subject to flow in the direction of the proximal end of the device.

2. The medical device of claim 1, wherein the first lumen comprises a central lumen for delivery of the plug removal fluid and the second lumen comprises an outer annular lumen for delivery of the plug-forming composition.

3. The medical device of claim 1, wherein the distal tip has a shape memory in a u-shape form.

4. The medical device of claim 1, wherein the distal tip comprises a plurality of exit ports each of which expels plug removal fluid in a proximal direction.

5. The medical device of claim 1, wherein the proximal end of the device comprises a luer lock fluid entry port.

6. The medical device of claim 1, wherein the proximal end of the device comprises a handle.

7. The medical device of claim 1, wherein the diameter of the device is dimensioned for insertion into a ureter.

8. The medical device of claim 7, wherein the device is between 1 and 4.5 Fr in diameter.

9. The medical device of claim 1, comprising a pull wire which is adapted to form a u-shaped distal tip for the device when pulled.

10. The medical device of claim 9, wherein the pull wire is disposed within a further lumen that extends along a portion of the length of the elongate body.

11. The medical device of claim 9, wherein the distal tip comprises a spring coil.

12. The medical device of claim 9, wherein the pull wire is attached to the spring coil.

13. A kit comprising (a) the medical device of claim 1 and (b) a pump.

14. A kit comprising (a) the medical device of claim 1 and (b) a guidewire.

15. A kit comprising (a) the medical device of claim 1 and (b) a reverse theitnosensitive polymer.

16. The kit of claim 15, wherein the reverse thermosensitive polymer is a block copolymer that comprises a polyoxyalkylene block.

17. The kit of claim 15, wherein the reverse thermosensitive polymer is a block copolymer that comprises polyoxyethylene, blocks, polyoxypropylene blocks, or both polyoxyethylene blocks and polyoxypropylene blocks.

18. A method comprising (a) positioning a medical device of within a body lumen that contains a polymeric plug, such that a distal tip of the device is positioned on a distal side of the polymeric plug, said medical device comprising an elongated body, a proximal end, said distal tip, and a lumen extending from the proximal end of the device to the distal tip of the device, wherein the proximal end of the device is adapted to engage a source of fluid, wherein the lumen is adapted to carry the fluid from the proximal end of the device to the distal tip of the device, and wherein the distal tip of the device is adapted to cause fluid emerging from the distal tip of the device to flow in the direction of the proximal end of the device and (b) forcing a plug removal fluid through the lumen and out the distal tip of the device such that fluid emerging from the distal tip of the device flows in the direction of the polymeric plug such that it dissolves the polymeric plug.

19. The method of claim 18, wherein the polymeric plug comprises a reverse thermosensitive polymer.

20. The method of claim 18, wherein the plug removal fluid is saline.

21. The method of claim 18, wherein the body lumen is a ureter.

* * * * *